US00PP37039P2

(12) United States Plant Patent
de Vos

(10) Patent No.: US PP37,039 P2
(45) Date of Patent: Oct. 21, 2025

(54) ***HYDRANGEA* PLANT NAMED 'HYLV19557'**

(50) Latin Name: *Hydrangea paniculata*
Varietal Denomination: HYLV19557

(71) Applicant: KWEKERIJ LENDERT de VOS B.V., Reeuwijk (NL)

(72) Inventor: Lendert de Vos, Reeuwijk (NL)

(73) Assignee: KWERKERIJ LENDERT de VOS B.V., Reeuwijk (NL)

( * ) Notice: Subject to any disclaimer, the term of this patent is extended or adjusted under 35 U.S.C. 154(b) by 0 days.

(21) Appl. No.: 19/030,050

(22) Filed: Jan. 17, 2025

(51) Int. Cl.
*A01H 5/02* (2018.01)
*A01H 6/48* (2018.01)

(52) U.S. Cl.
USPC ..... Plt./250

(58) Field of Classification Search
USPC ..... Plt./226, 250
See application file for complete search history.

(56) References Cited

U.S. PATENT DOCUMENTS

PP22,330 P2 * 12/2011 Wood ..... A01H 6/48
Plt./250

* cited by examiner

*Primary Examiner* — Karen M Redden
(74) *Attorney, Agent, or Firm* — C. Anne Whealy

(57) ABSTRACT

A new and distinct cultivar of *Hydrangea* plant named 'HYLV19557', characterized by its relatively compact, upright to broadly spreading plant habit; relatively moderately vigorous growth habit; freely branching habit; strong and sturdy stems; freely flowering habit; panicles with yellowish green-colored sterile flowers that become tinged with dark pink with subsequent development; and good postproduction longevity.

2 Drawing Sheets

Figure 1:
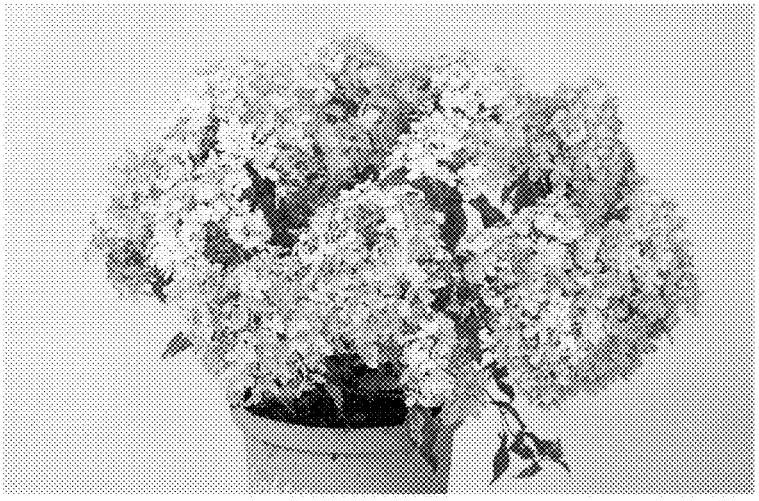

Botanical designation: *Hydrangea paniculata.*
Cultivar denomination: 'HYLV19557'.

CROSS-REFERENCED TO CLOSELY-RELATED APPLICATIONS:

A United Kingdom Plant Breeder's Rights application for this plant was filed by the Applicant/Assignee of the instant application, Kwekerij Lendert de Vos of Reeuwijk, The Netherlands on Aug. 20, 2024, application number 23/881, and published on Sep. 1, 2024. Foreign priority is not claimed to this United Kingdom Plant Breeder's Rights application.

A European Community Plant Breeder's Rights application for this plant was filed by the Applicant/Assignee of the instant application, Kwekerij Lendert de Vos of Reeuwijk, The Netherlands on Sep. 24, 2024, application number 2024/2232, and published on Dec. 15, 2024. Foreign priority is not claimed to this European Plant Breeder's Rights application.

BACKGROUND OF THE INVENTION

The present invention relates to a new and distinct cultivar of *Hydrangea* plant, botanically known as *Hydrangea paniculata,* commercially referred to as a Paniculated *Hydrangea* and hereinafter referred to by the name 'HYLV19557'.

The new *Hydrangea* plant is a product of a planned breeding program conducted by the Inventor in Reeuwijk, The Netherlands. The objective of the breeding program is to create new compact and strong *Hydrangea* plants with attractive inflorescences and good postproduction longevity.

The new *Hydrangea* plant originated from an open-pollination in August 2018 of *Hydrangea paniculata* 'HYLV02', disclosed in U.S. Plant Pat. No. 31,237, as the female, or seed, parent with an unknown selection of *Hydrangea paniculata* as the male, or pollen, parent. The new *Hydrangea* plant was discovered and selected as a single flowering plant from within the progeny of the stated open-pollination in a controlled greenhouse environment in Reeuwijk, The Netherlands in August 2019.

Asexual reproduction of the new *Hydrangea* plant by terminal vegetative cuttings since August 2019 in a controlled greenhouse environment in Reeuwijk, The Netherlands has shown that the unique features of this new *Hydrangea* plant are stable and reproduced true to type in successive generations of asexual reproduction.

SUMMARY OF THE NEW PLANT

Plants of the new *Hydrangea* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'HYLV19557'. These characteristics in combination distinguish 'HYLV19557' as a new and distinct *Hydrangea* plant:

1. Relatively compact, upright to broadly spreading plant habit.
2. Relatively moderately vigorous growth habit.
3. Freely branching habit.
4. Strong and sturdy stems.
5. Freely flowering habit.

6. Panicles with yellowish green-colored sterile flowers that become tinged with dark pink with subsequent development.
7. Good postproduction longevity.

Plants of the new *Hydrangea* can be compared to plants of the female parent, 'HYLV02'. Plants of the new *Hydrangea* differ primarily from plants of 'HYLV02' in the following characteristics:

1. Plants of the new *Hydrangea* are more compact than plants of 'HYLV02'.
2. Inflorescences of plants of the new *Hydrangea* are more broad than tall whereas inflorescences of plants of 'HYLV02' are more tall than broad.
3. Inflorescences of plants of the new *Hydrangea* are more open than and not as dense as inflorescences of plants of 'HYLV02'.

Plants of the new *Hydrangea* can be compared to plants of *Hydrangea paniculata* 'Jane', disclosed in U.S. Plant Pat. No. 22,330. In side-by-side comparisons, plants of the new *Hydrangea* differ primarily from plants of 'Jane' in the following characteristics:

1. Plants of the new *Hydrangea* are more compact than plants of 'Jane'.
2. Inflorescences of plants of the new *Hydrangea* are more open than and not as dense as inflorescences of plants of 'Jane'.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph at the top of the first sheet (FIG. 1) is a side perspective view of a typical flowering plant of 'HYLV19557' grown in a container.

Figure 2:
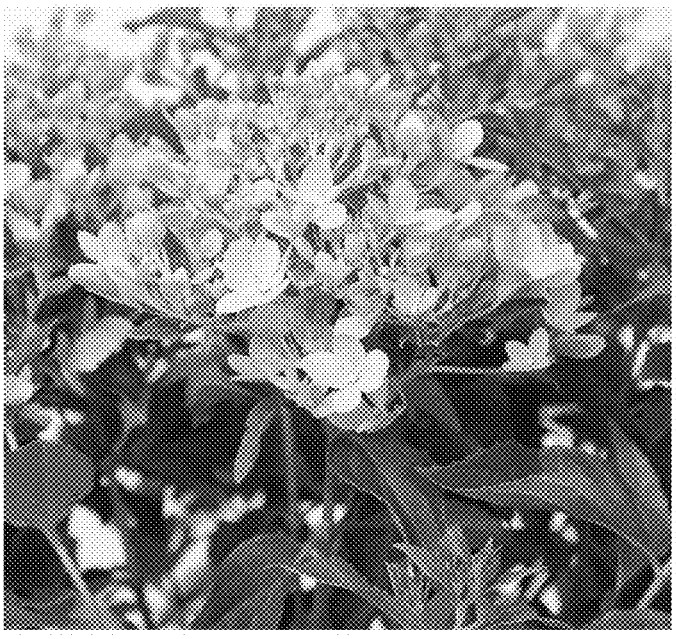

The photograph at the bottom of the first sheet (FIG. 2) is a close-up view of typical developing inflorescences of 'HYLV19557'.

Figure 3:
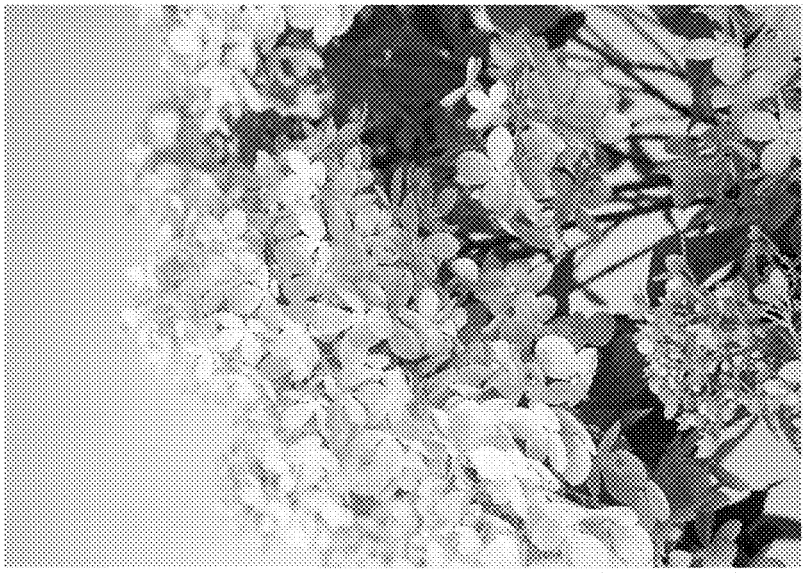

The photograph at the left of the second sheet (FIG. 3) is a close-up view of typical developed inflorescences of 'HYLV19557'.

Figure 4:
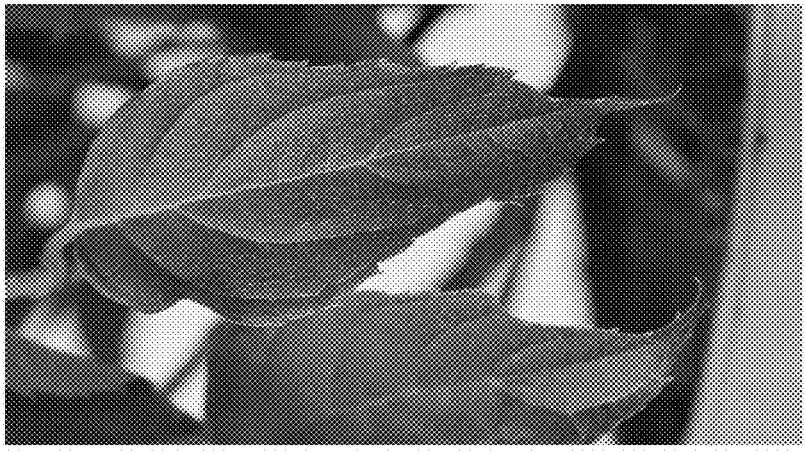

The photograph at the right of the second sheet (FIG. 4) is a close-up view of typical leaves of 'HYLV19557'.

DETAILED BOTANICAL DESCRIPTION

Plants used in the aforementioned photographs and in the following description were grown during the summer in 23-cm containers in an outdoor nursery in Reeuwijk, The Netherlands and under cultural practices typical of commercial *Hydrangea* production. During the production of the plants, day temperatures ranged from 18° C. to 32° C. and night temperatures ranged from 12° C. to 20° C. Plants of the new *Hydrangea* were two years old when the photographs and description were taken. In the following description, color references are made to The Royal Horticultural Society Colour Chart, Sixth Edition, except where general terms of ordinary dictionary significance are used. The new *Hydrangea* plant is not typically treated with aluminum sulfate to "blue" the flower color.

Botanical description: *Hydrangea paniculata* 'HYLV19557'.

Parentage:

*Female, or seed, patent.*—*Hydrangea paniculata* 'HYLV02', disclosed in U.S. Plant Pat. No. 31,237.

*Male, or pollen, patent.*—Unknown selection of *Hydrangea paniculata,* not patented.

Propagation:

*Type cutting.*—By vegetative terminal cuttings.

*Time to initiate roots, summer.*—About 16 days at temperatures ranging from 20° C. to 30° C.

*Time to produce a rooted young plant, summer.*—About four months at temperatures ranging from 20° C. to 30° C.

*Root description.*—Medium in thickness; fibrous; typically light brown in color, actual color of the roots is dependent on substrate composition, water quality, fertilizer type and formulation, substrate temperature and physiological age of roots.

*Rooting habit.*—Freely branching; dense.

Plant description:

*Plant and growth habit.*—Relatively compact; upright to broadly outwardly spreading and mounding plant habit; overall shape, flattened globular; strong and sturdy stems; relatively moderately vigorous growth habit and moderate growth rate; about one year from propagation are required to produce small finished plants.

*Plant height.*—About 35 cm.

*Plant diameter or area of spread.*—About 54.3 cm.

Lateral branch description:

*Branching habit.*—Freely branching habit with about 30 lateral branches developing per plant; pinching is not required, but will enhance lateral branch development.

*Length.*—About 18 cm.

*Diameter.*—About 3.5 mm.

*Internode length.*—About 3.7 cm.

*Strength.*—Strong, sturdy.

*Aspect.*—Erect to about 60° from vertical.

*Texture.*—Moderately pubescent; becoming woody with subsequent development.

*Color, developing.*—Close to 143C.

*Color, fully developed.*—Close to 199A; older bark, close to 199A, N199B and 200B.

*Lenticels.*—Density: Medium density. Length: About 1 mm. Diameter: About 0.75 mm. Color: Close to N170C.

Leaf description:

*Arrangement.*—Opposite or in whorls of three, simple.

*Length.*—About 7.8 cm.

*Width.*—About 4 cm.

*Shape.*—Elliptic to elliptic-ovate; moderately carinate.

*Apex.*—Apiculate.

*Base.*—Obtuse to acute.

*Margin.*—Mostly serrate; proximal 20% of margin, entire.

*Texture and luster, upper surface.*—Sparsely pubescent; slightly glossy.

*Texture and luster, lower surface.*—Moderately pubescent; slightly glossy.

*Venation pattern.*—Pinnate.

*Color.*—Developing leaves, upper surface: Close to 144A. Developing leaves, lower surface: Close to 146C. Fully developed leaves, upper surface: Close to 137B; venation, close to 146C. Fully developed leaves, lower surface: Close to 146B; venation, close to 146D.

*Petioles*.—Length: About 8 mm. Diameter: About 2 mm. Texture and luster, upper and lower surfaces: Sparsely pubescent; slightly glossy. Color, upper surface: Close to 146D; main vein, close to 143C. Color, lower surface: Close to 146B.

Flower description:

*Flower type and habit*.—Showy rotate sterile flowers and small, inconspicuous rotate fertile flowers arranged on terminal panicles; panicles broadly conical to roughly deltoid in shape; sterile flowers face upright, outwardly to slightly drooping and fertile flowers face mostly upright.

*Fragrance*.—None detected.

*Natural flowering season*.—Plants flower continuously for about three months; in garden in The Netherlands, plants flower from midsummer into the late summer.

*Flower longevity*.—Good postproduction longevity; sterile flowers maintain good substance for about six weeks on the plant, sterile flowers persistent; fertile flowers last for about five days on the plant, fertile flowers not persistent.

*Quantity of flowers*.—Freely flowering habit; about 175 sterile flowers per panicle and about 45 fertile flowers per panicle.

*Panicle height*.—About 13.4 cm.

*Panicle diameter*.—About 15 cm.

*Panicle peduncles*.—Length: About 11.2 cm. Diameter: About 2.5 mm. Strength: Moderately strong. Aspect: Primary peduncles, mostly erect; lateral peduncles, about 45° from primary peduncle axis. Texture and luster: Densely pubescent; matte. Color: Close to 193A.

*Sterile flower buds*.—Length: About 1 cm. Diameter: About 1.3 cm. Shape: Cup-shaped. Color: Close to 145B.

*Fertile flower buds*.—Length: About 4 mm. Diameter: About 3.5 mm. Shape: Broadly obovate. Color: Immature corolla, close to 145A and 145B and immature calyx, close to 145B.

*Sterile flower diameter*.—About 3.2 cm.

*Sterile flower depth* (*height*).—About 6 mm.

*Fertile flower diameter*.—About 8 mm.

*Fertile flower depth* (*height*).—About 5 mm.

*Petals, sterile flowers*.—Quantity and arrangement: Typically, four; occasionally three or five in a single whorl. Length: About 3 mm. Width: About 1.25 mm. Shape: Ovate; strongly concave. Apex: Acute. Base: Cuneate. Margin: Entire. Texture and luster, upper and lower surfaces: Smooth, glabrous; slightly glossy. Color: When opening, upper surface: Close to 154C. When opening, lower surface: Close to a blend of 145C and 150C. Fully opened, upper surface: Close to NN155A; distally, slightly tinged with close to 161D; color does not change with subsequent development. Fully opened, lower surface: Close to NN155A; distally, slightly tinged with close to 161C and 161D; color does not change with subsequent development.

*Petals, fertile flowers*.—Quantity and arrangement: Five in a single whorl. Length: About 3.5 mm. Width: About 1.75 mm. Shape: Ovate; moderately concave. Apex: Acute. Base: Cuneate. Margin: Entire. Texture and luster, upper and lower surfaces: Smooth, glabrous; slightly glossy. Color: When opening, upper and lower surfaces: Close to NN155A. Fully opened, upper surface: Close to NN155A; distally, slightly tinged with close to 161D; color does not change with subsequent development. Fully opened, lower surface: Close to NN155A; distally, slightly tinged with close to 161C and 161D; color does not change with subsequent development.

*Sepals, sterile flowers*.—Quantity and arrangement: Typically, four; occasionally three or five in a single whorl. Length: About 1.9 cm. Width: About 1.2 cm. Shape: Elliptic; slightly concave. Apex: Broadly and bluntly acute to obtuse with a minute and abrupt acute tip. Base: Cuneate. Margin: Entire to shallowly and finely serrate. Texture and luster, upper and lower surfaces: Smooth, glabrous; matte. Color: When opening, upper surface: Close to a blend of 145C and 150C, closest to 145C. When opening, lower surface: Close to a blend of 145C and 150C, closest to 150C. Fully opened, upper surface: Close to 145C; with subsequent development, color becoming closer to 150B tinged with close to 182C and 182D. Fully opened, lower surface: Close to 145C; with subsequent development, color becoming closer to 145C strongly tinged with close to 182D.

*Sepals, fertile flowers*.—Quantity and arrangement: Five in a single whorl. Length: About 2 mm. Width: About 1 mm. Shape: Broadly ovate. Apex: Acute. Base: Broadly cuneate. Margin: Entire. Texture and luster, upper and lower surfaces: Smooth, glabrous; matte. Color: When opening, upper and lower surfaces: Close to 145D. Fully opened, upper and lower surfaces: Close to 145D; color does not change with subsequent development.

*Pedicels, sterile flowers*.—Length: About 2.2 cm. Diameter: About 1 mm. Strength: Moderately strong. Aspect: About 20° to 60° from main peduncle axis Texture and luster: Moderately pubescent; matte. Color: Close to 145C.

*Pedicels, fertile flowers*.—Length: About 2 mm. Diameter: About 0.5 mm. Strength: Moderately strong. Aspect: About 5° from peduncle axis. Texture and luster: Moderately pubescent; matte. Color: Close to 145C.

*Reproductive organs, sterile flowers*.—Stamens: Quantity per flower: Eight. Filament length: About 2 mm. Filament color: Close to NN155D. Anther shape: Oblong. Anther length: About 0.3 mm. Anther color: Close to 155D. Pollen amount: Scarce. Pollen color: Close to 161C. Pistils: To date, pistil development has not been observed on sterile flowers.

*Reproductive organs, fertile flowers*.—Stamens: Quantity per flower: Eight. Filament length: About 3 mm. Filament color: Close to NN155D. Anther shape: Oblong. Anther length: About 0.3 mm. Anther color: Close to 155D. Pollen amount: Scarce. Pollen color: Close to 161C. Pistils: Pistil quantity per flower: Typically three; occasionally, two or four. Pistil length: About 2.5 mm. Stigma shape: Club-shaped.

Stigma color: Close to 157C. Style length: About 1.5 mm. Style color: Close to 145C. Ovary color: Close to 145B.

*Fruits and seeds*.—To date, fruit and seed development has not been observed on plants of the new *Hydrangea*.

Pathogen & pest resistance: Plants of the new *Hydrangea* have not been observed to be resistant to pathogens and pests common to *Hydrangea* plants.

Temperature tolerance: Plants of the new *Hydrangea* have been shown to be suitable for USDA Hardiness Zones 5 through 9.

It is claimed:

1. A new and distinct *Hydrangea* plant named 'HYLV19557' as herein illustrated and described.

* * * * *